United States Patent
Thenuwara et al.

(10) Patent No.: US 9,895,536 B2
(45) Date of Patent: Feb. 20, 2018

(54) THIN PROFILE COCHLEAR IMPLANTS

(71) Applicant: Advanced Bionics AG, Staefa (CH)

(72) Inventors: Chuladatta Thenuwara, Castaic, CA (US); Mark Downing, Valencia, CA (US); Kurt Koester, Los Angeles, CA (US); Stefan Menzl, Jona (CH)

(73) Assignee: Advanced Bionics AG, Staefa (CH)

( * ) Notice: Subject to any disclaimer, the term of this patent is extended or adjusted under 35 U.S.C. 154(b) by 28 days.

(21) Appl. No.: 14/889,381

(22) PCT Filed: May 10, 2013

(86) PCT No.: PCT/US2013/040640
§ 371 (c)(1),
(2) Date: Nov. 5, 2015

(87) PCT Pub. No.: WO2014/182316
PCT Pub. Date: Nov. 13, 2014

(65) Prior Publication Data
US 2016/0082249 A1    Mar. 24, 2016

(51) Int. Cl.
*A61N 1/36* (2006.01)
*A61N 1/05* (2006.01)
*A61N 1/375* (2006.01)

(52) U.S. Cl.
CPC ....... *A61N 1/36032* (2013.01); *A61N 1/0541* (2013.01); *A61N 1/375* (2013.01)

(58) Field of Classification Search
CPC ... A61N 1/36032; A61N 1/0541; A61N 1/375
USPC ......................................................... 607/57
See application file for complete search history.

(56) References Cited

U.S. PATENT DOCUMENTS

| | | | |
|---|---|---|---|
| 4,213,004 A * | 7/1980 | Acker | H01B 17/305 |
| | | | 174/151 |
| 6,272,382 B1 | 8/2001 | Faltys et al. | |
| 6,308,101 B1 * | 10/2001 | Faltys | A61N 1/08 |
| | | | 607/57 |
| 6,411,854 B1 | 6/2002 | Tziviskos et al. | |
| 8,027,735 B1 * | 9/2011 | Tziviskos | A61N 1/36032 |
| | | | 607/57 |
| 8,135,474 B1 | 3/2012 | Xie | |
| 8,538,530 B1 | 9/2013 | Orinski | |
| 2003/0050549 A1 | 3/2003 | Sochor | |
| 2004/0034368 A1 | 2/2004 | Pless et al. | |
| 2004/0176673 A1* | 9/2004 | Wahlstrand | A61N 1/3605 |
| | | | 600/377 |
| 2009/0143839 A1 | 6/2009 | Zimmerling | |
| 2010/0114249 A1 | 5/2010 | Wahlstrand et al. | |
| 2010/0204768 A1 | 8/2010 | Jolly et al. | |

(Continued)

FOREIGN PATENT DOCUMENTS

WO    2009139932 A1    11/2009

*Primary Examiner* — Carl H Layno
*Assistant Examiner* — Erin M Piateski
(74) *Attorney, Agent, or Firm* — Fabian VanCott; Steven Nichols (57) ABSTRACT

A thin profile impact resistant cochlear implant includes a single piece machined case having a bottom surface, wherein at least a portion of the bottom surface is concave and a single piece machined cover configured to be joined to the case, the cover comprising a convex upper surface. A method for forming thin profile cochlear implant is also provided.

21 Claims, 10 Drawing Sheets

(56) References Cited

U.S. PATENT DOCUMENTS

| | | | | |
|---|---|---|---|---|
| 2010/0274309 A1* | 10/2010 | Knipfer | .................. | A61N 1/375 607/36 |
| 2010/0292760 A1* | 11/2010 | Leigh | ................... | A61N 1/3754 607/57 |
| 2011/0266713 A1 | 11/2011 | Vincent et al. | | |
| 2012/0016444 A1* | 1/2012 | Koester | ................ | A61N 1/3754 607/57 |
| 2012/0221078 A1* | 8/2012 | Leigh | ................... | A61N 1/3754 607/57 |

* cited by examiner

Fig. 8

THIN PROFILE COCHLEAR IMPLANTS

CROSS-REFERENCE TO RELATED APPLICATION

This application is the U.S. National Phase under 35 U.S.C. § 371 of International Application No. PCT/US2013/040640, filed on May 10, 2013, the disclosures of which are incorporated by reference herein.

BACKGROUND

Cochlear implant systems can be used to provide a sense of hearing to deaf or severely hard of hearing patients. Cochlear implant systems typically include an external portion and an implanted portion. The implanted portion includes an electrode array that is inserted into the cochlea. The is external portion senses environmental sound and transmits electrical signals representing the sound to the implanted portion. The electrode array in the implanted portion directly simulates nerves in the patient's cochlea to produce a sense of hearing.

BRIEF DESCRIPTION OF THE DRAWINGS

The accompanying drawings illustrate various examples of the principles described herein and are a part of the specification. The illustrated examples are merely examples and do not limit the scope of the claims.

Throughout the drawings, identical reference numbers designate similar, but not necessarily identical, elements.

DETAILED DESCRIPTION

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples.

Figure 1:
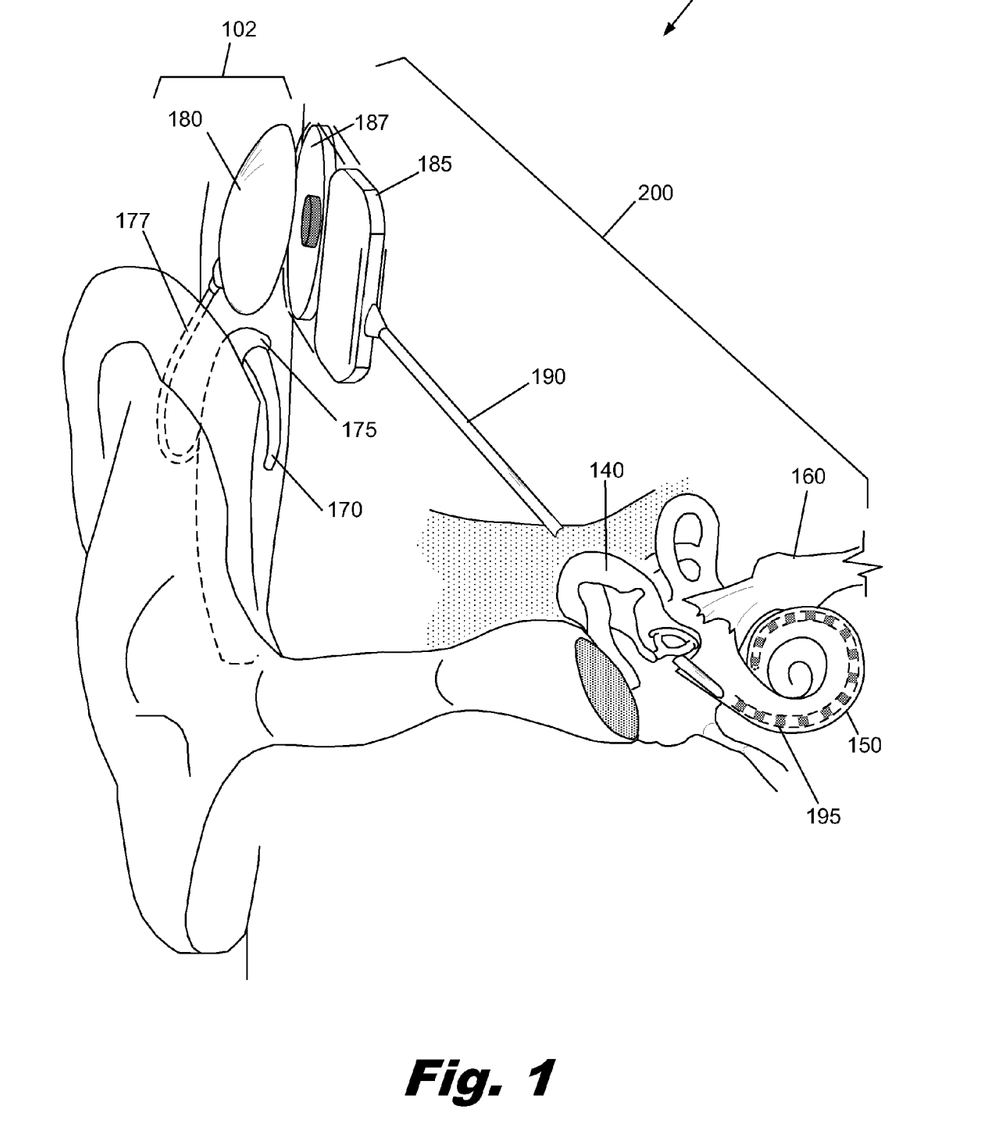
FIG. 1 is a diagram showing one illustrative example of a cochlear implant system that includes an internal implanted portion and an external portion, according to one example of principles described herein.

FIG. 1 is a diagram showing one illustrative example of a cochlear implant system (100) that includes an internal implanted portion (200) and an external portion (102). The cochlear implant (100) provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

The external portion (102) of the cochlear implant system (100) can include a Behind-The-Ear (BTE) unit (175), that contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the BTE unit (175) and transmits them to the implanted antenna assembly (187) by electromagnetic transmission.

Figure 2A:
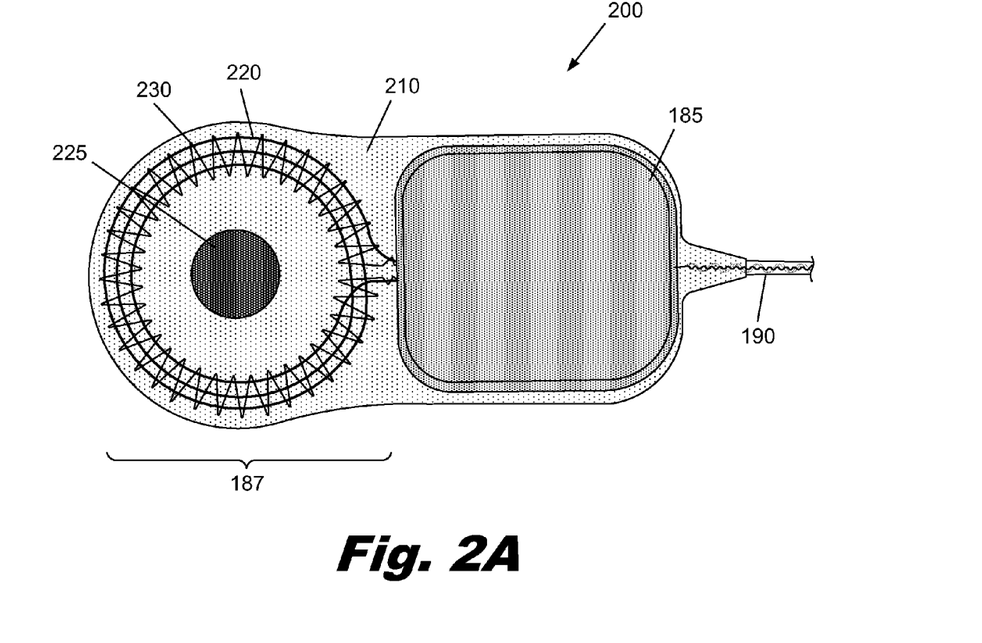
FIG. 2A is a top view of part of the implanted portion of a cochlear implant, according to one example of principles described herein.

The internal implanted portion (200) of the cochlear implant includes an electrode array (195) that is surgically placed within the patient's cochlea. Unlike hearing aids, the cochlear implant (100) does not amplify sound, but works by directly stimulating any functioning auditory nerve cells inside the cochlea (150) with electrical impulses representing the ambient acoustic sound. This bypasses the defective cochlear hair cells that normally transduce acoustic energy into electrical energy. The implanted portion (200) of the cochlear implant system is shown in FIG. 1 in its implanted configuration and in FIG. 2 before implantation. The internal portion (200) of the cochlear implant (100) includes an internal processor (185), an antenna assembly (187), and a cochlear lead (190) having an electrode array (195). The internal processor (185) and antenna assembly (187) are secured beneath the user's skin, typically above and behind the external ear (110). The antenna assembly (187) receives signals and power from the transmitter (180). The internal processor (185) receives these signals and operates on the signals to generate modified signals. These modified signals are then sent through the cochlear lead (190) to the electrode array (195), which is at the distal portion of the cochlear lead (190) and is implanted within the cochlea (150). The electrode array uses the modified signals to provide electrical stimulation to the auditory nerve (160).

Figure 2B:
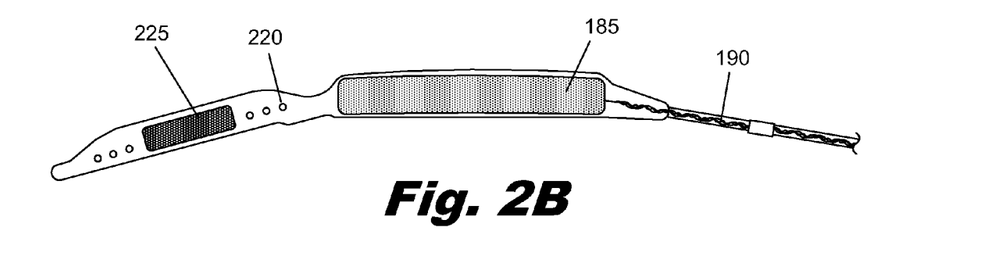
FIG. 2B is side view of the implanted portion shown in FIG. 1A, according to one example of principles described herein.

FIG. 2A is a top view of part of the implanted portion (200) of a cochlear implant (100, FIG. 1). The implanted portion (200) includes the antenna (187) and the processor (185). In this example, the antenna (187) is external from the processor (185). The antenna (187) includes a spiral coil (220) that is surrounded by a shield wire (230). A magnet (225) is disposed in the center of the antenna (187). The magnet (225) removably secures the transmitter (180, FIG. 1) over the antenna (187). The antenna (187) is connected to the processor (185). An electrode lead (190) is connected to the opposite side of the processor (185). The entire assembly is covered with encapsulation (210). FIG. 2B is side view of the implanted portion shown in FIG. 2A. The side view shows the processor (185), magnet (225), antenna coil (220), and lead (190). In one example, the thickness of this assembly is less than 5 millimeters.

Figure 3:
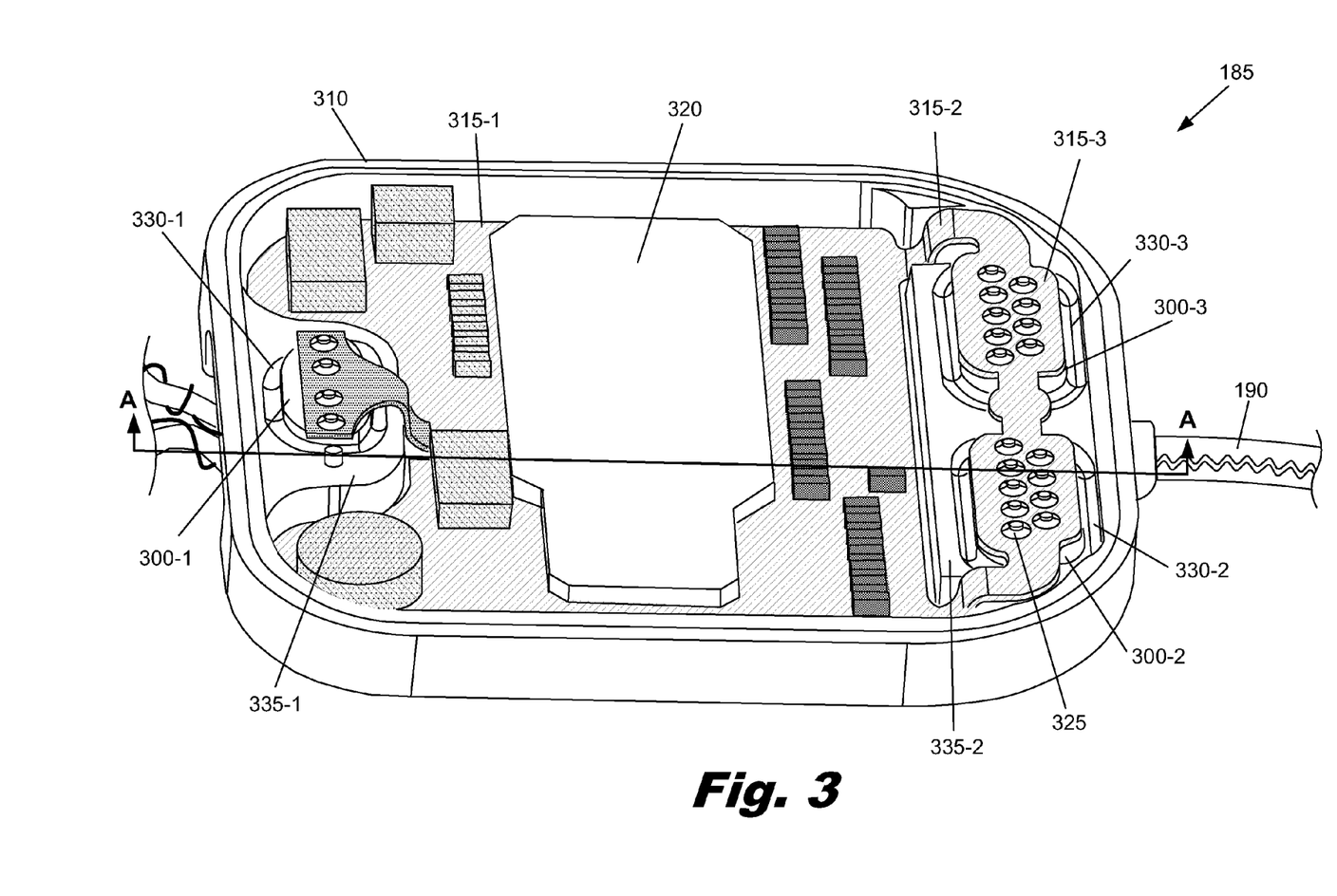
FIG. 3 is a perspective view of a processor with its cover removed, according to one example of principles described herein.

FIG. 3 is a perspective view of a processor (185) with its cover removed to show its internal components. In this example, the processor (185) includes a case (310), three feedthroughs (300), a flex circuit (315) that connects to the feedthroughs (300) and a variety of electronics (320) connected to the flex circuit (315). The case (310) of the processor (185) can be formed from a variety of materials, including biologically compatible metals such as titanium. For example, the case (310) may be machined from a single piece of titanium. Titanium is a biologically compatible metal with high strength and resilience. Titanium is also impermeable to fluids and gasses.

As described in more detail below, the feedthroughs (300) are sealed into apertures in the case (310). In this implementation, there are 18 pins available for connection to signal or ground wires in the electrode lead (190). These pins are divided into two groups of 9 in separate feedthroughs (300-2, 300-3). The feedthroughs (300-2, 300-3) are made up impermeable ceramic bodies with conductive pins that pass through the ceramic bodies. The pins can have a variety of geometries and be sealed into the ceramic using a variety of techniques. In this example, the pins have a circular cross section and are brazed/soldered into holes in the ceramic body. In other examples, the pins may be ribbon-like conductors that are formed into the ceramic body before the ceramic is fired. While these ceramic bodies are very strong in compression, they are weaker in tension. When bending forces are applied to a ceramic body, one side of the ceramic body is placed in compression while the other side of the ceramic body is placed in tension. The side in tension tends to fracture. There are several principles that are applied in the present embodiment to mitigate fractures in the ceramic body of feedthroughs. First, the ceramic body can be constructed with materials, reinforcement, and internal geometry that tends to reduce cracking, inhibit crack growth, and to prevent propagation of the cracks through the ceramic body by controlling the crack trajectory.

Other principles that can be used to increase the robustness of the feedthrough (300) include isolating the feedthrough (300) from stresses. In this implementation, the feedthroughs (300) are surrounded by grooves (330). These grooves (330) create thin cross sections ("flexures") in the case (310) that partially isolate the feedthroughs stresses applied to the case (310). These flexures allow the more robust case to resist applied stresses without stresses experienced by the feedthrough exceeding the tensile strength of the ceramic. The flexures are described in greater detail below.

The size and shape of the feedthrough (300) also influences the robustness of the ceramic body. For example, feedthroughs with high aspect ratios (high length-to-width ratios and/or high width-to-thickness ratios) have a greater tendency to fail. In the example shown in FIG. 3, there are 18 pins that can be connected to the electrode lead (190). These 18 pins could be formed in a single feedthrough (300). However, in the processor (185) shown in FIG. 3, this would result in a long narrow feedthrough (300) that may have an increased tendency to fracture. By separating the 18 pins into two different feedthroughs (300-2, 300-3) with 9 pins each, the aspect ratio of each of the ceramic bodies in the feedthroughs (300-2, 300-3) becomes significantly closer to one. For example, the feedthroughs (300-2, 300-3) may have a length-to-width aspect ratio of less than 3:1. The width-to-thickness ratio of the feedthroughs (300-2, 300-3) may also be less than 3:1. In one embodiment, the length-to-width ratio of the signal feedthroughs (300-2, 300-3) are approximately 2.5:1 and width-to-thickness ratio is approximately 2:1. These relatively low aspect ratios result in blocky ceramic bodies that resist higher levels of stresses with a decreased probability of fracturing. In one example, the thickness is measured through the feedthrough along an axis parallel to the conductors, the length is the greatest linear dimension measured along an edge of the feedthrough, and the width is measured across the feedthrough in a direction that orthogonal to the length and thickness measurements.

The antenna feedthrough (300-1) also has a length-to-width ratio and a width-to-thickness ratio that are both less than 3:1. In the illustrated embodiment, the antenna feedthrough has a length-to-width ratio of less than approximately 2:1 and a width-to-thickness ratio of less than 1.5:1.

The case surrounding the feedthroughs includes walls (335-1, 335-2). The upper surfaces of the walls can be contacted by ribs in the cover (see FIGS. 4A and 4B) to form internal support columns.

Connection portions of the flex circuit (315-3) fit over the feedthroughs (300) and connect to pins extending from the interior side of the feedthroughs (300). In this example, the connections (325) on the flex circuit (315) are joined to the feedthrough pins by any of a variety of methods, such as soldering, conductive epoxy or the like. Lead portions of the flex circuit (315-2) join the connection portions of the flex circuit (315-3) to the main portion of the flex circuit (315-1) where the electronic components (320) are mounted. The connection portions of the flex circuit (315-3) and the main component portion of the flex circuit (315-1) are in parallel offset planes.

Figure 4A:
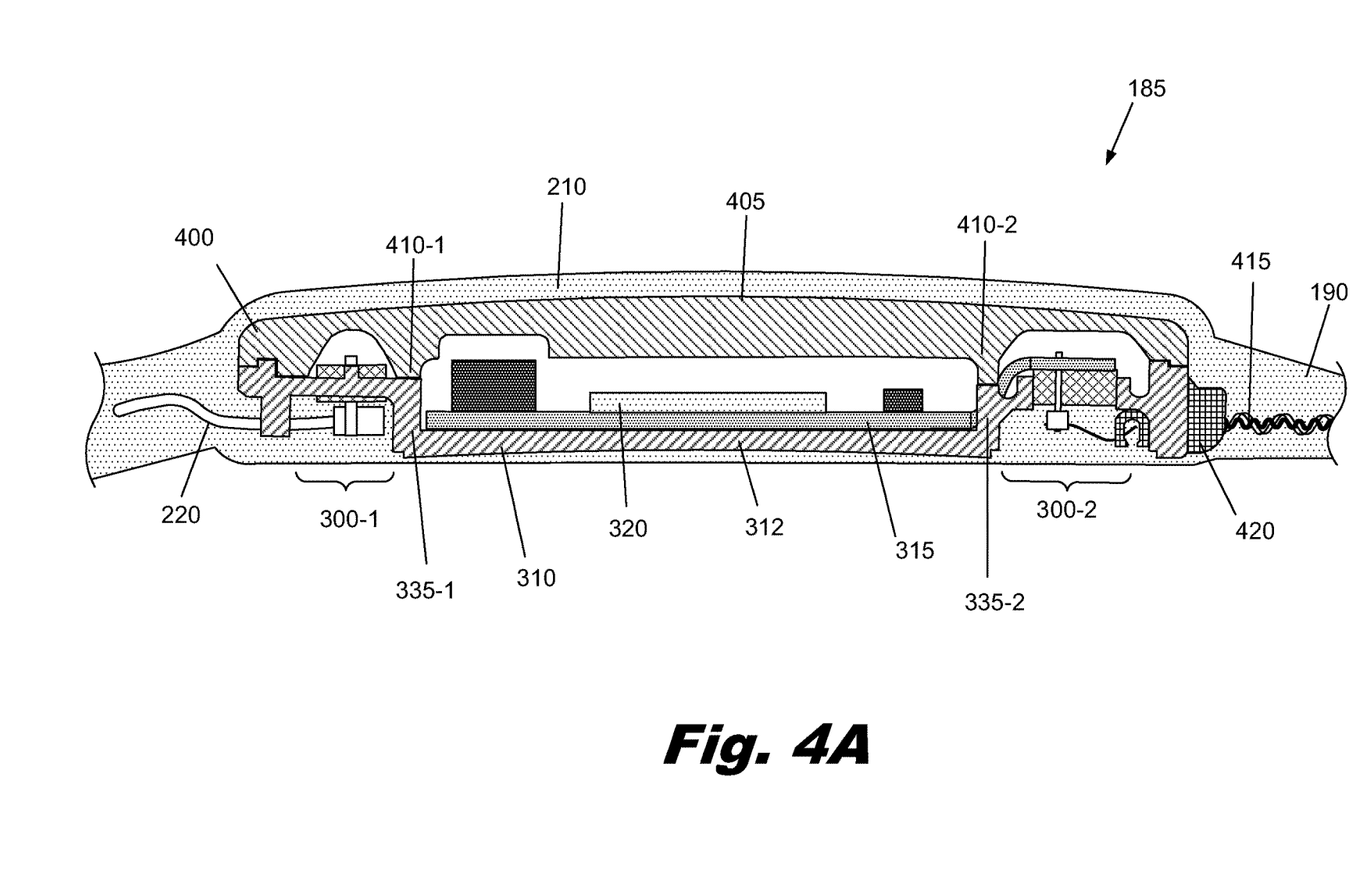
FIGS. 4A and 4B are side cross sectional views of an implanted processor, according to one example of principles described herein.

FIG. 4A is a side cross sectional view of the processor (185) shown in FIG. 3. The cross section is taken along line A-A in FIG. 3. FIG. 4 shows the hermetic housing that is made up of the case (310), feedthroughs (300) sealed into the case (310), and a cover (400) that is hermetically joined to the case (310). This protects the electronics (320) mounted on the flex circuit (315) from the fluids and gasses present in the implanted environment as well as from impacts and other stresses. The electrode lead (190) extends from the opposite side of the processor (185). The signal wires (415) in the electrode lead pass through a wire carrier (420) and into an internal cavity where they are connected to the feedthrough (300-2). The entire processor (185), antenna coil (220), and electrode lead (190) are covered by an encapsulant (210) such as medical grade silicone.

As discussed above, the processor (185) is implanted between the scalp and the skull. The processor (185) and antenna (187, FIG. 2A) may be held in place between the scalp and the skull in a variety of ways, including creating a bone bed, creating a periostial pocket, suturing the processor (185) in place or other technique. In general, the case (310) is implanted facing the patient's skull and the cover (400) is on the opposite side facing away from the skull. When an external impact or other force is applied to the processor (185), the load typically contacts the cover (400), transferred into the case (310) and then transferred into the patient's skull. The cover (400) and case (310) include a number of features that are designed to increase the impact robustness of the implant while maintaining its low profile. These features are designed to protect the electronic components/connections and maintain the hermeticity of the processor (185).

The cover (400) is designed to absorb and distribute impact forces while protecting the interior components. In this example, parts of the cover (400) are significantly thicker than the case (310). The cover (400) may be manufactured from a number of materials, including machined titanium. Clearance areas are formed in the cover (400) to accommodate components mounted in the case (310). For example, clearance areas are machined into the single piece of titanium that makes up the cover (400) over the feedthroughs (300) and high profile electronic components. The upper surface of the processor (185) may be a convex arch. The convex arch increases the strength of the cover (400) in resisting impact or other external forces.

One of these features is the presence of walls (335) in the case (310) that extend from the lower surface (312) of the case (310) to an upper interface surface (405) of the cover (400). Support ribs (410) formed in the cover (400) extend downward to join with the walls (335) at the upper interface surface (405). The walls (335) are inside the processor (185) perimeter and shorten the length of the unsupported span of the cover (400). The combination of the support ribs (410) and the walls (335) create a solid metal support column that extends from the upper interface surface (405) of the cover (400) to the skull of the patient. These support columns are designed to directly transfer impact loads to the patient's skull. Further, because the support columns reduce the span of the cover (400), the cover (400) can be thinner and lighter without compromising the integrity of the processor (185).

The lower surface (312) of the case (310) may be concave. This may serve a number purposes, including allowing the case (310) to conform to the skull of the patient for a lower profile, more comfortable fit. However, the concave lower surface (312) may also serve a structural purpose. The concave lower surface (312) lifts the middle of the case (310) away from the skull. This prevents the skull from exerting large forces in the middle of the case (310) and allows the case (310) to be thinner. The forces are transmitted through the support columns to the skull. In this example, the support columns are placed around the perimeter of the lower concave portion (312) of the case (310). The support columns formed by interfacing features of the cover and case can be designed in a variety of other locations to support the integrity of the processor As shown in below in FIG. 4B, the concave portion only covers a portion of the lower surface (312) of the case (310), with the perimeter of the concave portion ending proximal to the support columns (455). In one example, the support columns (455) are adjacent to the feedthroughs (300, FIG. 4A), but separated from the feedthroughs (300, FIG. 4A) by a groove that creates a thin cross section flexure in the case (310) that isolates the feedthroughs (300, FIG. 4A) from forces that are transmitted through the support column (455). The support columns (455) are also separate from the perimeter interface between the cover (400) and the case (310). This reduces the unsupported span of the cover (400) and increases the robustness of the processor (185).

Figure 4B:
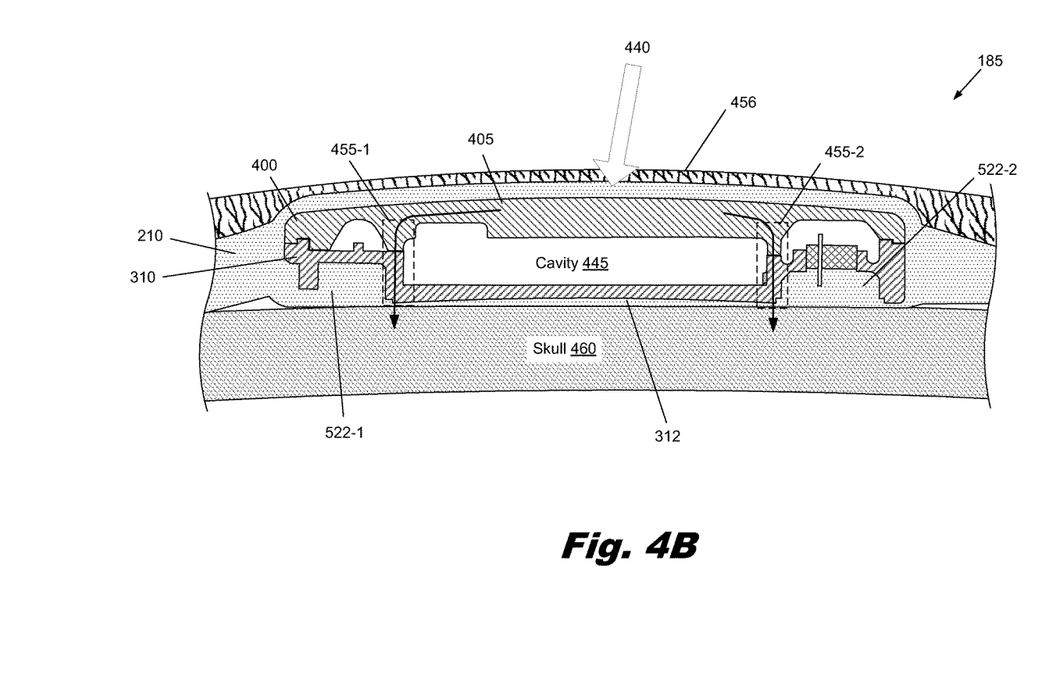

FIG. 4B shows the processor (185) in place between the skin (456) and the skull (460). For simplicity, a number of components have been omitted from FIG. 4B, including the flex circuit, wires, connections, electronics and other components. FIG. 4B shows an external impact force (440) that is applied to the processor (185). In most cases, when an impact force (440) is applied to the processor (185), the processor (185) distributes the force over a broader area and reduces the likelihood of injury to the skull (460). The external impact force (440) may arise from a variety of circumstances in the course of the patient's life, including playing sports, falling, or being involved in an automobile accident. The skin (456) and encapsulation (210) may serve to partially cushion and distribute the impact force (440). The force is then applied to the convex upper surface (405) of the cover (400). This arched surface strongly resists flattening because its ends are secured at the perimeter and there are intermediate support columns (455) that shorten the unsupported span of the cover (400). These metal support columns (455) structurally transfer the force through the processor (185) and into the skull (460). This is shown by the black arrows passing radially outward from the impact forces and passing downward through the support columns (455) to the skull (460). The impact force (440) may also be distributed to the skull (460) through the processor (185) perimeter. The pins and feedthroughs (300, FIG. 4A) are protected from these impact forces because they are located within internal recesses (522). The grooves (330, FIG. 3) further isolate the feedthroughs from the impact forces.

Figure 5A:
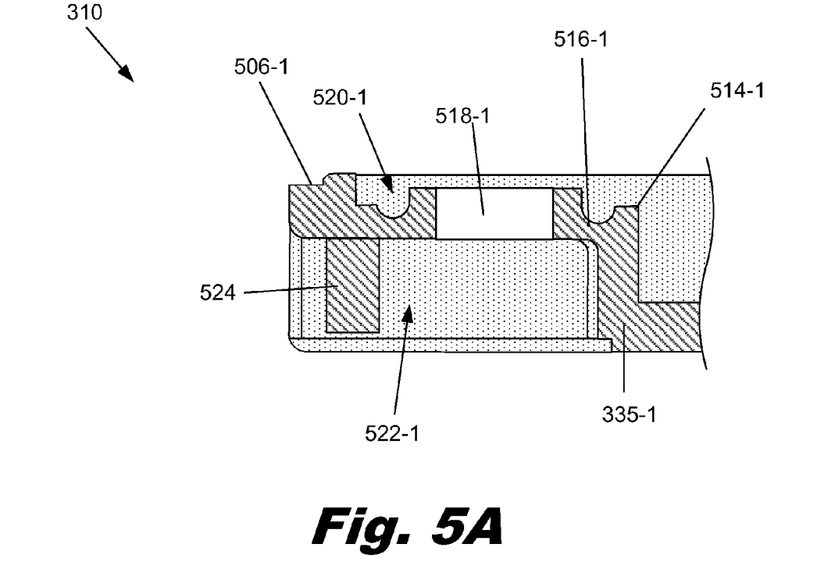
FIG. 5A is partial side cross sectional view of the implanted processor shown in FIG. 3, according to one example of principles described herein.
Figure 5B:
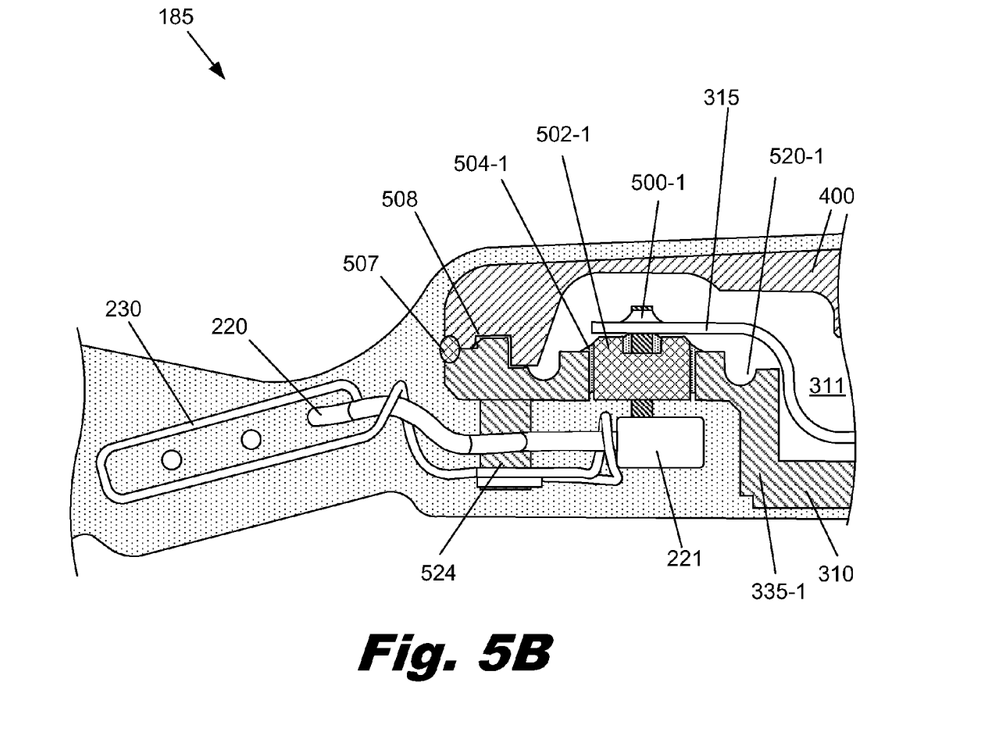
FIG. 5B is a partial side cross sectional view of the processor case, according to one example of principles described herein.

FIGS. 5A and 5B show more detailed cross sectional views of the antenna side of the case and processor, respectively. FIG. 5A shows a cross section of the case (310). As discussed above, the entire case (310) can be machined from a single piece of titanium. In this example, a contoured aperture (518-1) has been formed to receive the feedthrough (300, FIG. 4A). In some examples, the apertures may include contours with specific cutouts to receive braze, corner reliefs for the edges of the ceramic, a shelf to contact the outer (lower) face of the ceramic body to hold it in the desired position before brazing, and other features. The braze joint may include gold, TiCuNi, TiNi, partially transient liquid phase material or fully transient liquid phase material. The aperture (518-1) is formed within a recess (522-1). The walls (335-1) of the recess (522-1) surround the feedthrough (300, FIG. 4A) to provide protection for the feedthrough pins that extend into the recess (522), wires and connections between the pins and wires. In this example, one wall (335-1) becomes part of the support column (455, FIG. 4B), with the top of the wall serving as the upper contact interface (514). The corresponding rib of the cover (400, FIG. 4B) rests on the upper contact surface to form the support column (455, FIG. 4B). The aperture (518-1) is a surrounded by a groove (520-1). The groove (520-1) forms a reduced cross section flexure (516-1) that isolates/reduces the stresses transmitted from the case (310) to the feedthrough. A portion of the stress is reduced by the thinner cross section flexure (516-1) deflection. This portion of the case (310) also includes a perimeter contact surface (506-1) that interfaces with the perimeter of the cover (400, FIG. 4B). An antenna grounding post (524) is formed in the recess (522-1). The shield wires are connected to these grounding posts (524). The grounding post (524) may also serve as a barrier to protect the connections to the feedthrough from impact or intrusion.

FIG. 5B shows a cross sectional diagram of the antenna side of the processor in its operational configuration. The ceramic body of the feedthrough (502-1, 500-1) is brazed in place in the aperture to form a hermetic seal (504-1) between the ceramic body and the case (310). The cover (400) is welded to the case (310) around the perimeter. For example, laser welding may be used to create a hermetic weld joint (507) around the perimeter of the processor (185, FIG. 4A) where the cover (400) and the case (310) form an interface (508). The feedthrough, case (310), and cover (400), when hermetically joined, form a sealed interior cavity (311) that protects the electronics (320, FIG. 3).

As discussed above, the antenna coil (220) receives power and signals from the exterior transmitter. The antenna coil (220) is connected to two feedthrough pins (500-1) via connection blocks (221). A shield wire (230) is wrapped around the antenna coil (220) to eliminate unwanted electrical interference. The shield wire (230) is connected to the case (310) via an antenna grounding post (524). The feedthrough pins (500-1) extending out of the ceramic body (502-1) and the exterior electrical connections can be particularly vulnerable to impacts. In this design, the feedthrough pins (500-1) extend out of the ceramic body (502-1) into the recess (522-1, FIG. 5A). The connections between the antenna coil (220) and the feedthrough pins (500-1) are made within the recess (522-1, FIG. 5A) and inside the profile of the processor (185, Fig.). The recess walls (335-1) and grounding posts (524) surrounding the recess (522-1, FIG. 5A) protect these connections. If an external force is applied to the processor, the walls, and potentially the grounding posts can withstand the force and prevent damage to the connections and pins. The walls (335-1) around the recess (522-1) also form part of the support column. The portion of the walls that contact the ribs on the cover are not shown in this view because the ribs contact the support walls on either end of the feedthrough (see FIG. 4B) and the cross section is taken through the center of the antenna feedthrough. The groove (520-1) that creates flexure around the feedthrough is also shown. The flex circuit (315) is shown connected to the feedthrough.

The interface (508) between the case (310) and the cover (400) has a locking geometry that substantially prevents the outward radial motion of the cover (400). This can be important during impact events to prevent the weld (507) from being overstressed. The locking interface (508) includes a central protrusion on the case (310) with a matching indentation between two lips in the case (310). In this example, the two lips have different heights. When the case (310) and cover (400) are joined together, the interface (508) can be used to transfer loads from the cover (400) to the case (310). This can be particularly useful when a large impact load is applied to the arched cover. The impact will have a tendency to flatten the arch, which pushes the perimeter of the cover (400) radially outward. The locking interface (508) allows the case (310) to resist this outward force and prevent undesirable deflection of the cover (400). The ceramic feedthrough is partially isolated from these forces by the groove/flexure (520-1). The flexure tends to slightly bend or distort when excess force is applied. This reduces the force transmitted to the feedthrough and its braze joint (504-1). Reducing this force reduces the chances for failure or weakening of the braze joint (504-1), pins (500-1), and ceramic body (502-1). In some examples, a separate cover can be placed over the recess to further protect the connections.

The use of a flex circuit (315) within the processor further isolates the electronics from physical forces while still providing robust electrical connections. Very little force can be transmitted through the compliant materials that make up the flex circuit (315) to the electronics (320, FIG. 3). For example, the flex circuit (315) may include flexible polyamide or other suitable backing films/coatings. The "S" shaped geometry of the lead portion of the flex circuit provides additional flexibility to the flex circuit (315).

Figure 6A:
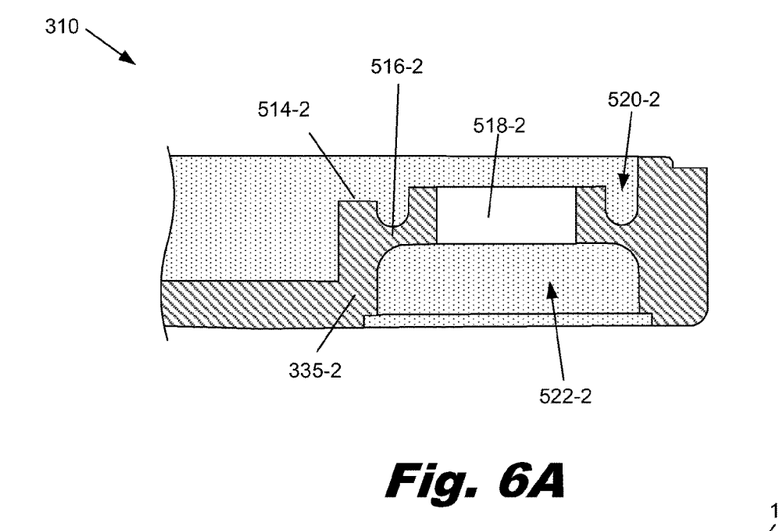
FIG. 6A is partial side cross sectional view of the implanted processor shown in FIG. 4, according to one example of principles described herein.

FIG. 6A shows the electrode feedthrough side of the case (310). The electrode feedthrough side of the case includes two apertures (518) to receive the electrical feedthroughs that connect to the electrode signal wires. The cross sectional plane in FIG. 6A passes through only one of these apertures (518-2). These apertures (518) are formed in the upper surface of a recess (522-2). The walls (335-2) of the recess form the lower parts of the outer perimeter wall and the support column (455, FIG. 4B) in the processor. In between these structural walls and the aperture (518), a groove (520-2) creates a reduced cross section flexure (516-2) that partially isolates the aperture (518) and flexure (516-2) from applied forces. A portion of the upper surface of the wall (335-2) forms a rib contact area (514-2). As was discussed above with respect to FIG. 4A, a support rib on the cover contacts the rib contact surface and forms a support column (455-2, FIG. 4B).

Figure 6B:
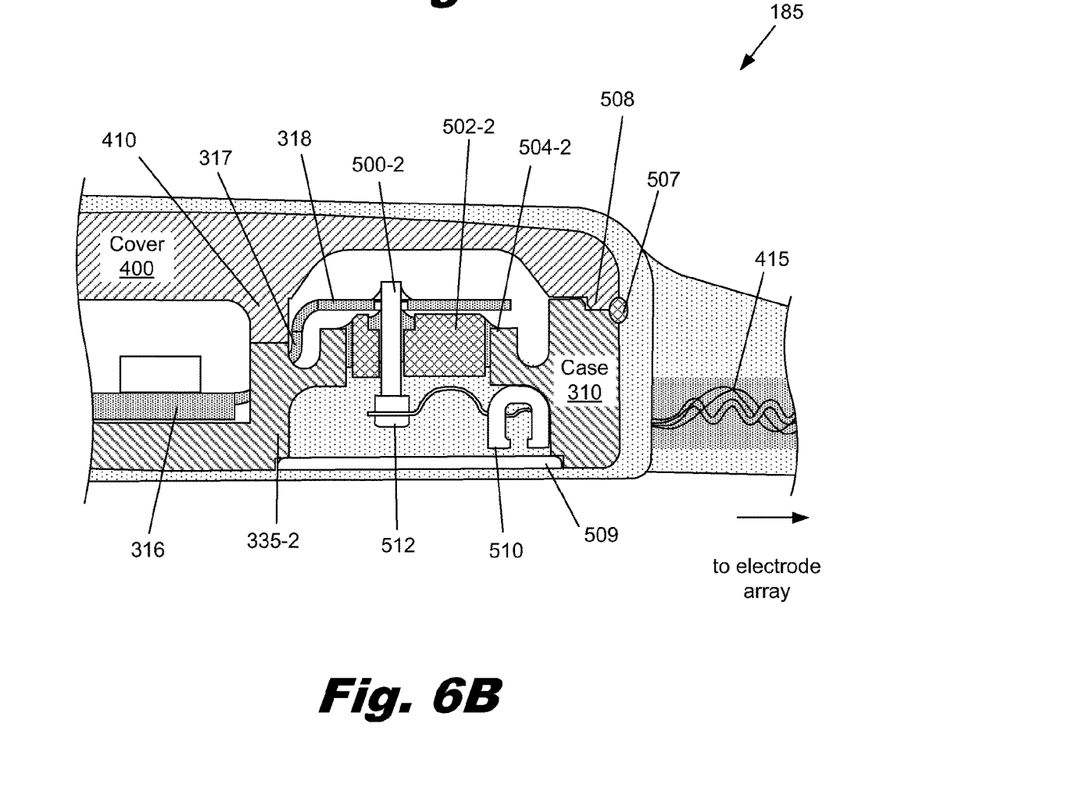
FIG. 6B is a partial side cross sectional view of the processor case, according to one example of principles described herein.

FIG. 6B shows the right portion of the processor (185) and the connections between the processor and the electrode lead. As discussed above, the ceramic body (502-2) of the feedthrough is sealed into the aperture using a braze joint (504-2). Feedthrough pins (500-2) extend out of both sides of the ceramic body (502-2). In some embodiments, the feedthrough pins (500-2) are also brazed into the ceramic body (502-2) with a braze joint (504-2). The connection portion of the flex circuit (318) is connected to the interior side of the pins (500-2). This forms electrical connections between the pins (500-2), the lead portion (317) and component portions of the flex circuit (316).

The connection to the signal wires (415) is made by placing the signal wires (415) in a wire carrier (510) that routes each wire to the desired pin (500-2). Connections (512) are then made between the signal wires (415) and the pins (500-2). These connections (512) are formed in the recess (522-2, FIG. 6A) so that they are inside the profile of the processor and protected by the walls (335-2) of the recess. In some examples, a cover (509) is placed over the recess to further protect the connections (512). As discussed above, the wall surrounding the recess (335) includes a portion that interfaces with a rib (410) in the cover (400) to form the interior support column (455-2, FIG. 4B).

Figure 7A:
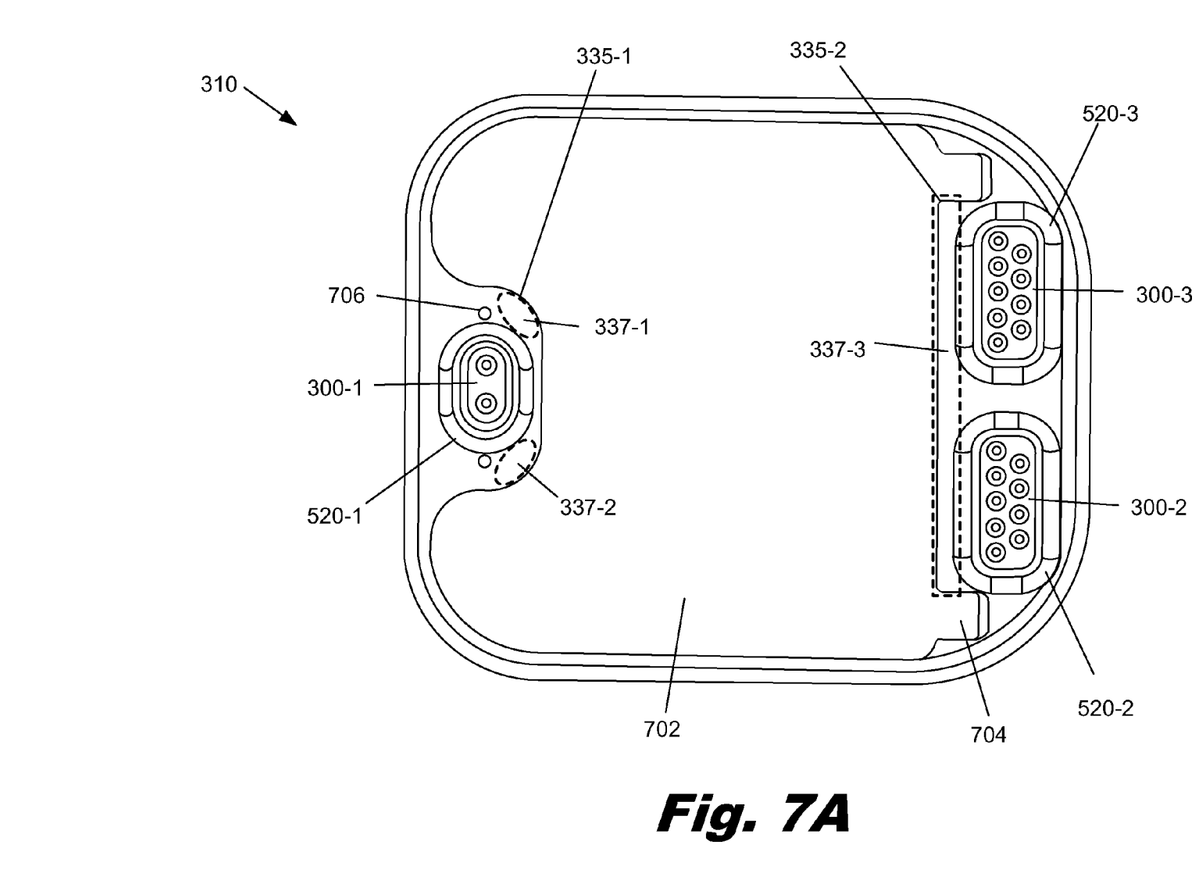
FIG. 7A is a top view of the processor case and feedthroughs, according to one example of principles described herein.

FIG. 7A shows a top view of the interior side of the case (310) with the antenna feedthrough (300-1) and electrode feedthroughs (300-2, 300-3) in place. The case (310) is machined from one monolithic piece of metal. Forming the case (310) from multiple pieces would necessitate additional joints that could become failure points in the design.

A main cavity (702) separates the antenna feedthrough (300-1) on the left from the electrode feedthroughs (300-2, 300-3) on the right. The input signals are received through the antenna feedthrough (300-1) and processed by electronics contained in the main cavity (702). The processed signals are output to the electrode array via the electrode feedthroughs (300-2, 300-3) on the right. The flex circuit (315, FIG. 5B) electrically connects the various components. The main cavity (702) includes cutouts for the flex circuit connecting portions (704) on either side of the electrode feedthroughs (300-2, 300-3).

Each of the feedthroughs is surrounded by a groove (520) that forms a thin cross section flexure to partially isolate the feedthroughs (300) from stresses in the rest of the case (310). As discussed above, portions of the upper surfaces of the walls (335) interface with the cover. Examples of these interface areas (337) are identified in FIG. 7A.

Figure 7B:
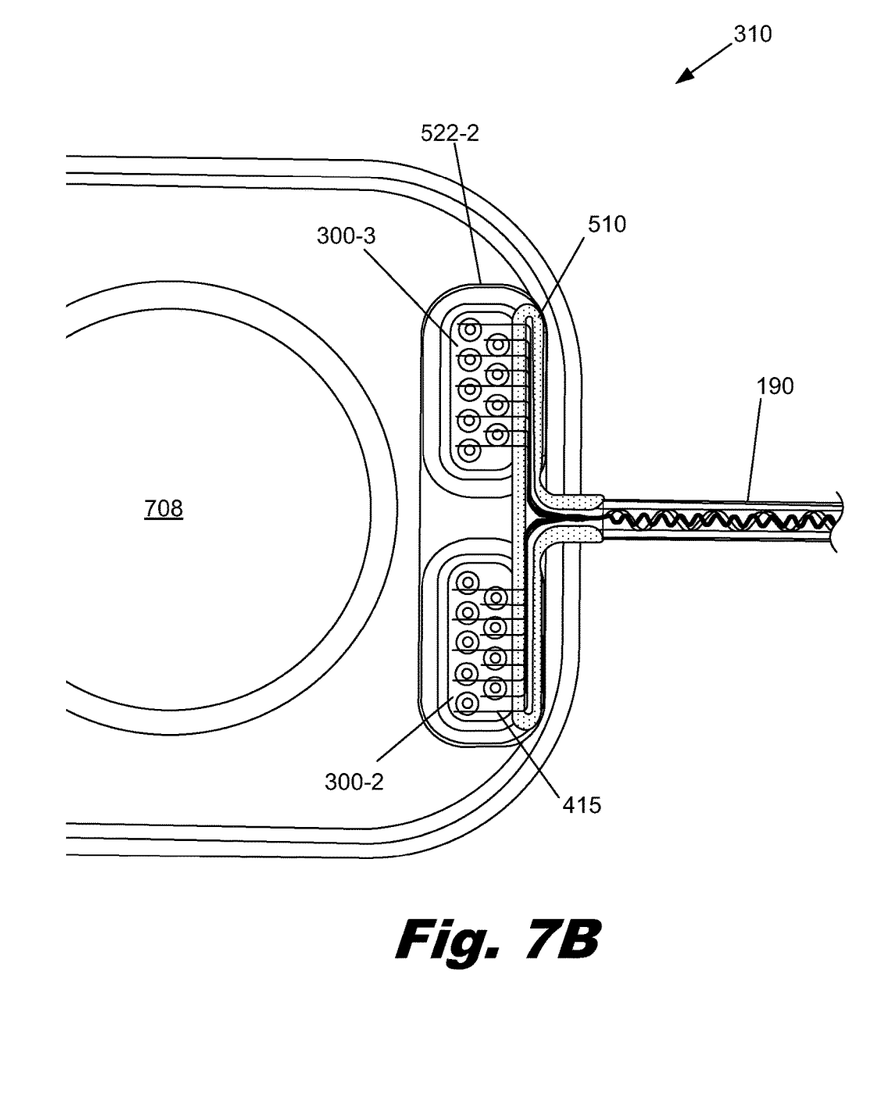
FIG. 7B is a bottom view of the processor case, feedthroughs and cochlear lead, according to one example of principles described herein.

FIG. 7B shows a plan view of a portion of the bottom of the case (310) with feedthroughs (300) in place within the recess (522-2) and the wire carrier (510) distributing signals wires (415) from the electrode lead (190) to the various pins in the feedthroughs.

In this example, the concave area (708) on the bottom of the case (310) is circular and located in the center of the case (310). As discussed above, the concave area (708) lifts the center of the case (310) away from the skull and allows other portions of the case (310) to be in more direct contact with the skull. In particular, the portions of the processor that contain the support columns may be in more direct contact with the skull than the center of the case or the perimeter of the case.

Figure 8:
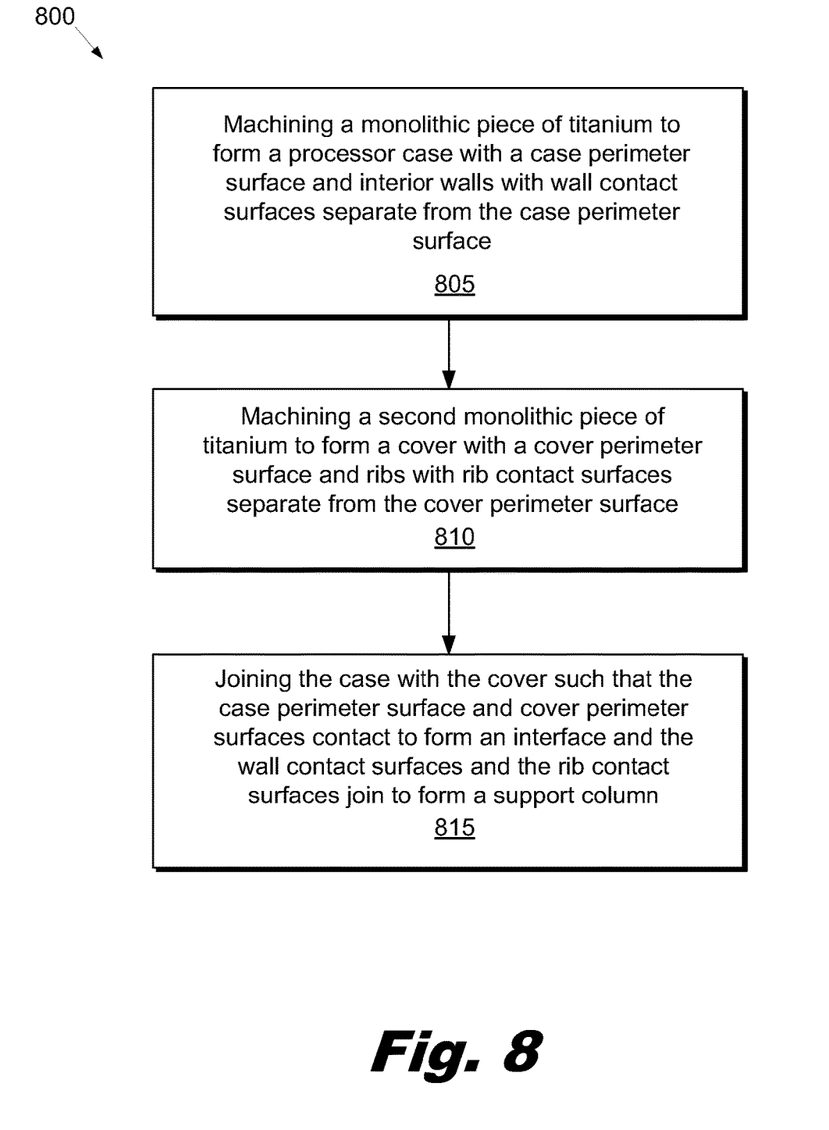
FIG. 8 is a flow chart of a method for making a hermitically sealed processor, according to one example of principles described herein.

FIG. 8 is a flow chart of a method for making a hermitically sealed processor. The method includes machining a first monolithic piece of titanium to form processor case with a case perimeter surface and interior walls with wall contact surfaces separate from the case perimeter surface (block 805). The machining may also include forming a main cavity, recesses on an opposite side from the main cavity, apertures in the recesses, walls around the recesses and a perimeter interface. Feedthroughs are sealed into the apertures using hermetic joints. For example, the feedthroughs may be sealed into the apertures using a braze joint. Grooves can be cut around the apertures to form thinner cross section flexures that reduce stresses transmitted to the feedthroughs.

A second monolithic piece of titanium is machined to form a cover with a cover perimeter surface and ribs and rib contact surfaces separate from the cover perimeter surface (block 810). The case is joined with the cover such that the case perimeter surface and the cover perimeter surfaces contact to form a perimeter interface and the wall contact surfaces and the rib contact surfaces contact to form at least one support column (block 815). The edges of the perimeter interface can be welded to form a hermetic seal between the cover and case.

The preceding description has been presented only to illustrate and describe examples of the principles described. This description is not intended to be exhaustive or to limit these principles to any precise form disclosed. Many modifications and variations are possible in light of the above teaching. The features shown and/or described in connection with one figure may be combined with features shown and/or described in connection with other figures.

What is claimed is:

1. A cochlear implant comprising:
a single piece machined metal case having a bottom surface, wherein at least a portion of the bottom surface is concave, and the concave portion of the bottom surface has a smaller radius of curvature than a skull at an implant site such that the concave portion of the bottom surface is separated from the skull;
a single piece machined cover configured to be joined to the case, the cover comprising a convex upper surface, wherein the case and cover form an enclosure of the cochlear implant.

2. The cochlear implant of claim 1, wherein the case comprises an interior wall extending from the bottom surface to a wall interface surface; the cover comprising a corresponding rib extending from the convex upper surface to a rib interface surface; and the case includes an aperture to accommodate a feedthrough, wherein the interior wall is adjacent to the feedthrough.

3. The cochlear implant of claim 2, further comprising a weld joining a perimeter interface between the case and cover and the wall interface surface and the rib interface surface contact to form a support column extending from the convex upper surface to the bottom surface.

4. The cochlear implant of claim 3, wherein the support column is separate from the perimeter.

5. The cochlear implant of claim 3, further comprising a feedthrough hermetically sealed in the aperture, wherein pins of the feedthrough are oriented parallel to a smallest side of the case, the perimeter is on a first side of the feedthrough, and the support column is on an opposite side of the feedthrough.

6. The cochlear implant of claim 5, wherein the aperture is formed in a wall of a recess, such that pins of the feedthrough sealed in the aperture are inside the recess and inside the profile of a processor.

7. The cochlear implant of claim 1, further comprising:
a perimeter interface between the case and cover;
interior support columns configured to reduce an unsupported span length of cover and to transfer impact force from the cover through the case.

8. The cochlear implant of claim 7, wherein the interior support columns are located proximal to an edge of the concave portion of the bottom surface.

9. The cochlear implant of claim 1, further comprising:
a first feedthrough comprising a ceramic body with pins passing through the ceramic body; and
wherein the case further comprises:
a recess with walls;
an aperture in the recess surrounded by the walls, the aperture to receive the first feedthrough, wherein the walls surrounding the first feedthrough extend beyond the pins such that the first feedthrough is entirely within the recess; and
a strain relief groove surrounding the aperture to isolate the first feedthrough from applied forces, the strain relief groove unoccupied by any portion of the implant when the first feedthrough is connected to an electrode array.

10. The cochlear implant of claim 9, further comprising a flex circuit comprising:
a connection portion to connect pins extending from an interior side of the first feedthrough;
a component portion whereon electrical components are mounted;
a lead portion connecting the connection portion to the component portion, wherein the connection portion and component portion are in offset planes.

11. The cochlear implant of claim 9, further comprising:
a second feedthrough; and
an electrode array connected to the pins in the first and second feedthrough, wherein a smaller size of the first and second feedthrough increase the robustness of the cochlear implant against impact when compared to a single long feedthrough.

12. The cochlear implant of claim 9, wherein a length-to-width aspect ratio of the ceramic body is less than 3:1.

13. The cochlear implant of claim 9, wherein a width-to-thickness aspect ratio of the ceramic body is less than 3:1.

14. A hermetically sealed electronic housing comprising:
a feedthrough comprising a ceramic body with pins passing through the ceramic body; and
a single piece feedthrough case comprising:
a recess with walls;
an aperture in the recess surrounded by the walls, the aperture for receiving the feedthrough, wherein the walls surrounding the feedthrough extend beyond the pins such that the feedthrough is entirely within the recess; and a strain relief groove surrounding the aperture to isolate the feedthrough, wherein the strain relief groove is filled with fluid when the feedthrough is connected to an electrode array.

15. The housing of claim 14, wherein at least a portion of the walls around the feedthrough contact a cover and reduce the unsupported span length of the cover, the walls contacting the cover at an edge of the cover and at a separate non-edge of the cover.

16. The housing of claim 14, wherein the feedthroughs are vertically mounted such that the pins are oriented approximately normal to a skull when implanted in a patient.

17. The housing of claim 14, wherein the housing has a thickness less than of 5 millimeters.

18. A cochlear implant comprising:
a single piece case comprising:
  a bottom surface, wherein at least a portion of the bottom surface is concave;
  at least one interior wall extending from the bottom surface to a wall interface surface;
  a recess;
  an aperture in the recess; and
  a groove surrounding the aperture to form a reduced cross section flexure around the aperture, where the groove is free of material of the implant when the implant is connected to an electrode array; and
an electrical feedthrough hermetically sealed in the aperture, wherein the feedthrough comprises a length-to-width aspect ratio less than approximately 2.5:1 and a width-to-thickness ratio less than approximately 2:1;
a single piece cover configured to be joined to the case, the cover comprising:
  a convex upper surface;
  a rib corresponding to an interior wall, the rib extending from the convex upper surface to a rib interface surface wherein the rib interface surface and the wall interface surface join to form a support column extending from the convex upper surface of the cover to the bottom surface of the case, wherein the support column is separate from a perimeter interface between the case and the cover with the perimeter interface on a first side of the feedthrough and the support column is on an opposite side of the feedthrough; and
a weld around on perimeter interface hermetically joining the case to the cover.

19. A method for forming a cochlear implant comprising:
machining a first monolithic piece of titanium to form a processor case with a case perimeter surface and interior walls with wall contact surfaces separate from the case perimeter surface, a portion of a bottom surface of the case being concave;
machining a second monolithic piece of titanium to form a cover, wherein the cover comprises a perimeter surface and ribs with contact surfaces separate from the perimeter surface; and
joining the case with the cover such that the case perimeter surface and the cover perimeter surface to form a perimeter interface and the wall contact surfaces and the rib contact surfaces contact to form at least one support column over the concave portion of the bottom surface such that an impact applied to the cover produces elastic deflection in the cover and the concave portion of the bottom surface of the case, the support column transmitting the impact from the cover to the concave portion of the bottom surface of the case.

20. The method of claim 19, wherein machining the case further comprises forming:
a main cavity;
recesses on an opposite side from the main cavity;
apertures in the recesses; and
grooves around the apertures to form flexures surrounding the apertures, wherein the grooves are on an interior surface of the cavity.

21. The method of claim 20, further comprising brazing feedthroughs into the apertures, wherein the flexures reduce stresses transmitted to the feedthroughs.

* * * * *